United States Patent
Martinant et al.

(10) Patent No.: US 10,745,697 B2
(45) Date of Patent: Aug. 18, 2020

(54) METHOD FOR PERFORMING MULTIPLEXED GENOTYPING

(71) Applicant: Limagrain Europe, Saint-beauzire (FR)

(72) Inventors: Jean-Pierre Martinant, Vertaizon (FR); Pascal Flament, Aubiere (FR)

(73) Assignee: LIMAGRAIN EUROPE, Saint-Beauzire (FR)

( * ) Notice: Subject to any disclaimer, the term of this patent is extended or adjusted under 35 U.S.C. 154(b) by 179 days.

(21) Appl. No.: 15/110,660

(22) PCT Filed: Jan. 9, 2015

(86) PCT No.: PCT/EP2015/050313
§ 371 (c)(1),
(2) Date: Jul. 8, 2016

(87) PCT Pub. No.: WO2015/104364
PCT Pub. Date: Jul. 16, 2015

(65) Prior Publication Data
US 2016/0326522 A1    Nov. 10, 2016

(30) Foreign Application Priority Data

Jan. 11, 2014  (EP) ..................................... 14305043

(51) Int. Cl.
*C12Q 1/68*     (2018.01)
*C12N 15/10*    (2006.01)
*C12Q 1/6827*   (2018.01)
*C12Q 1/6806*   (2018.01)

(52) U.S. Cl.
CPC ..... *C12N 15/1093* (2013.01); *C12N 15/1065* (2013.01); *C12Q 1/6806* (2013.01); *C12Q 1/6827* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

PUBLICATIONS

The definition of "bijection" from en.wikipedia.org. Printed on Dec. 6, 2019.*
Agrigenomics Genotyping Decision Reach a Crossroads, Application Spotlight: Analyzing Genetic Variation (May 17, 2013).
Badke et al., *Methods of tagSNP selection and other variables affecting imputation accuracy in swine*, 14(8) BMC Genetics 14 Pages (2013).
Crossa et al., *Genomic Prediction in Maize Breeding Populations with Genotyping-by-Sequencing*, 3 Genomic Selection 1903-1926 (Nov. 2013).
Dassonneville et al., *Short Communication: Imputation performances of 3 low-density marker panels in beef and dairy cattle*, 95(7) J. Dairy Sci. 4136-4140 (2012).
Habier et al., *Genomic Selection Using Low-Density Marker Panels*, 182 Genetics 343-353 (May 2009).
Khatkar et al., *Strategies and utility of imputed SNP genotypes for genomic analysis in dairy cattle*, 13(538) BMC Genomics 12 Pages (2012).
VanRaden et al., *Genomic evaluations with many more genotypes*, 43(10) Genetics Selection Evolution 11 Pages (2011).
Weigel et al., *Prediction of unobserved single nucleotide polymorphism genotypes of Jersey cattle using reference panels and population-based imputation algorithms*, 93 J. Dairy Sci. 2229-2238 (2010).
Zhang et al., *Marker imputation with low-density marker panels in Dutch Holstein cattle*, 93 J. Dairy Sci. 5487-5494 (2010).
International Search Report and Written Opinion dated Mar. 23, 2016, in corresponding PCT Application No. PCT/EP2015/050313.

* cited by examiner

*Primary Examiner* — Frank W Lu
(74) *Attorney, Agent, or Firm* — Panitch Schwarze Belisatio & Nadel LLP

(57) ABSTRACT

The invention relates to a method for genotyping individuals, through multiplexing genotyping, when samples carrying different loci of various individuals are pooled and genotyping is performed on this pool.

15 Claims, 3 Drawing Sheets

METHOD FOR PERFORMING MULTIPLEXED GENOTYPING

CROSS-REFERENCE TO RELATED APPLICATIONS

This application is a U.S. National Stage Application pursuant to 35 U.S.C. § 371 of International Patent Application PCT/EP2015/050313, filed on Jan. 9, 2015, and published as WO 2015/104364 on Jul. 16, 2015, which claims priority to European Patent Application 14305043.3, filed on Jan. 11, 2014, all of which are incorporated herein by reference in their entireties for all purposes.

The invention relates to a method for genotyping individuals, through multiplexing genotyping, where samples carrying different loci of various individuals are pooled and genotyping is performed on this pool.

The genotyping of a few markers per sample and of 10 000 markers (or more) per sample can be addressed with a very good efficiency with platforms like the SNPline™ from Kbioscience on one hand and the Affymetrix Axiom® platform or the Next Generation sequencing based Genotyping (NGG) on the other hand.

Nevertheless, these systems may not be the most effective ones for use in breeding applications especially when genotyping is done on progenies of sister plants, which have a high Linkage Disequilibrium (non-random association of alleles at two or more loci).

Next Generation sequencing based Genotyping (NGG) are new genotyping methods developed with the leverage of the Next Generation sequencing methods and the reduced cost of sequencing associated. Next Generation sequencing methods are summarized in the review of Jay Schendure and Hanlee Ji (Nature Biotechnology, Vol 26, No 10 Oct. 2008); 454 sequencing from Roche, Marlulies et al., (Nature vol 437 p 376-380, 2005), Illumina Solexa (Fedurco et al., NAR 34, e22 (2006) and Tarcatti et al., NAR 36, e25 (2008), AB SOLiD from Applied Biosystem (Shendure et al., Science 309, 1728-1732 (2005), HeliScope (Braslaysky et al., PNAS 100, 3960-3964(2003)). NGG may address this genotyping application, using the huge capacity of current sequencer and assuming that several hundreds of samples can be sequenced in a single run for example after a DNA library preparation based on the TruSeq™ custom Amplicon protocol. But the main limitation of such protocol is based on the requirement to add a tag per sample which is currently the only way to redistribute each sequence/data to the corresponding sample. This tagging step is, at the time being, a bottleneck in term of high throughput and cost for NGG approach and is difficult to conceptualize for array based protocols, due to the nature of the added tag, which is currently not easily detectable by an array.

The purpose of the invention is to provide a new genotyping method that allows the genotyping of several individuals without the need of indexing each individual independently.

Definitions

An "allele" is one of a number of alternative forms of the same gene or same genetic locus.

A "locus" is the specific location of a gene or DNA sequence or position on a chromosome.

A "molecular marker" or "marker" is a gene or DNA sequence with a known location on a chromosome for which different alleles can be revealed through the use of molecular protocols. It can be a short DNA sequence, such as a sequence surrounding a single base-pair change (single nucleotide polymorphism, SNP), or a long one, like microsatellites.

In summary, a marker makes it possible to discriminate between different alleles at a specific locus. Use of markers to do so in an individual consists in genotyping said individual (see below). An individual for which the alleles at different loci have been determined is said to be a "genotyped individual" for the markers associated with these loci.

An "ordered set of markers" is a set of markers wherein each marker is genetically positioned as compared to the other markers. In other words, the relative (genetic) position or order of each marker with regards to the others is known. Said ordered set of markers may be represented by a list of markers in which each marker, in the list, is genetically localized just after the marker before it in the list, and just before the marker listed after it.

There may obviously be different lists of markers in case the set of markers is intended for genotyping of different DNA segments (such as different chromosomes).

The markers of said ordered set of markers may be evenly distributed over the DNA region to genotype, or not. The set of markers is preferably a high density set of markers (which means at least one marker every 5 cM on average), and there can be markers with a higher density, for the specific and precise genotyping of some regions.

"Genotyping" means determining the combination of alleles for one marker or a set of markers. In the context of the present invention, genotyping may be performed on the whole genome of an individual, on a part of the genome, such as on one or more chromosomes, on a part of one or more chromosomes, or on one or more specific regions of the genome.

In order to genotype an individual (or part of the genome of an individual), one uses a set of markers. By extension, sequences that may be polymorphic between different individual can be named "markers" (it is clear that polymorphism for a given marker can be observed between a specific individual and a second individual, whereas it would not be observed with a third individual). These markers can thus indicate the nature of an allele at the specific locus that they target.

For markers that differentiate between two alleles, and assuming that the frequency of both alleles is balanced, it is statistically assumed that about 50% of the markers will reveal the same allele, between two unrelated individuals, just by chance.

An individual is said to be "derived from a cross between parents" if the parents of said individuals are known. Said individual may be the direct progeny or descendant of the sexual crossing of the parents, at the first generation or at a following generation.

An individual is said to be "related to a population" (or "apparented to a population" or "kin to a population") if it descends (belongs to the progeny) from sexual crosses between individuals of said population, at the first generation, or between individuals being the progeny of said population (at a later generation).

A "related population" (or apparented population) is a population comprising individuals that have strong linkage disequilibrium between two consecutive markers/alleles. Individual in a related population generally share common ancestors. Methods for calculating linkage disequilibrium are known in the art and are described, for instance in the lecture Lecture 15 (Bio 107/207, Winter 2005, Linkage disequilibrium and recombination, available from University of California San Diego: http://bio.classes.ucsc.edu/bio107/Class%20pdfs/W05_lecture15.pdf)

"Consecutive markers" are markers that are located consecutively in an ordered set of markers defining a chromosome map. On a following list of genetically ordered markers mk1, mk2, mk3, mk4, examples of consecutive markers are mk1 and mk2, mk2 and mk3, mk3 and mk4.

As an example of linkage disequilibrium, let's take 2 consecutive alleles (1A and 1B at position 1 and 2A and 2B at position 2), with each allele having a 50% prevalence.

In a non-related population, since individuals in this population don't share common ancestors, if an individual presents allele 1A at position 1 and allele 2A at position 2, another individual that presents allele 1A at position 1 will have a 50% probability to have allele 2A at position 2 and a 50% probability to have allele 2B at position 2.

In a related population, there is a strong linkage disequilibrium between two consecutive markers, which means that, in most frequent cases, if an individual presents allele 1A at position 1 and allele 2A at position 2, another individual that presents allele 1A at position 1 will have a stronger probability than 50% to have allele 2A at position 2. Indeed, the fact that the two individual share a common ancestor, there is a non-random association of alleles at these two loci, that descend from a single, ancestral chromosome.

Means for Genotyping an Individual

Genotyping an individual is generally performed in two steps, the first step being the preparation of DNA of said individual and the second step being the "identification" of the alleles at the marker loci.

Preparation of DNA (Extraction)

For performing DNA extraction on plants, generally a plant tissue that could be a leaf sample or a seed sample, is first grinded by using for instance the Geno/Grinder® (SPEX® SamplePrep®, Metuchen, N.J., USA). The flour is then submitted to a lysis buffer and a purification step is performed to eliminate other cell constituents and keep the DNA. One protocol based on CTAB lysis buffer is described in Rogers and Bendich (1994, Extraction of DNA from plant, fungal and algal tissues. In: Gelvin S B, Schilperoort R A (eds) Plant Molecular Biology Manual).

The method as described above can be described as the "conventional way" to prepare DNA.

Identification of the Alleles

Once the DNA has been prepared, the nature of the alleles at molecular markers is identified (or "revealed") by different methods.

One of the method should be the Kaspar method from KBioscience (LGC Group, Teddington, Middlesex, UK). The KASP™ genotyping system uses tree target specific primers: two primers, each of them being specific of each allelic form of the SNP (Single Nucleotide Polymorphism) and one other primer to achieve reverse amplification, which is shared by both allelic form. Each target specific primer also presents a tail sequence that corresponds with one of two FRET probes: one label with FAM® dye and the other with HEX® dye.

Successive PCR reactions (cycles of amplification) are performed The nature of the emitted fluorescence is used to identified the allelic form or forms present in the mix from the studied DNA.

Another method that can be used is the AXIOM® method from Affymetrix (Santa Clara, Calif., USA): this method makes use of a high density array comprising hundreds or thousands of probes arrayed on a small chip, allowing for many SNPs to be interrogated simultaneously.

The probes may:
  Carry the polymorphisms. In this case, for a given allele, the array will bear the probes corresponding to all different allele forms
  Be probes that are close to the polymorphism. In this case, the nature of the allele is revealed through primer extension The DNA of the individual to be genotyped is amplified through linear amplification, for example using degenerated primers. After amplification, the DNA is enzymatically fragmented into short (25 to 125 bp) fragments.

These fragments are purified, re suspended and hybridized to the array. Following hybridization, the array is washed under stringent conditions to remove non-specific hybridization. Each bound nucleotide is queried via a multi-color ligation event carried out on the array surface (solution probe bearing attachment site for one of two dyes depending of the 3'SNP site base hybridize to the glass plobe/target complex). After ligation the arrays are stained and imaged.

Sequencing methods may also be used for genotyping an individual. One can use any technology in the art, such as the one described in the paper "Agrigenomics genotyping Decisions Reach a crossroads", Application spotlight: Analysing Genetic Variation", available on the Illumina (San Diego, Calif., USA) website. (http://res.illumina.com/documents/products/appspotlights/app_spotlight_ngg_ag.pdf)

The method according to the invention uses the fact that one can take advantage of the pre-existing knowledge of the genotyping information of the individuals of a second population, when genotyping individuals of a first population that is related to said second population.

Once the genotyping information is obtained for an individual according to the method of the invention, one can allocate (input), for said individual, the alleles at the loci that have not been genotyped (the loci corresponding to the markers that were not associated with the subgroup to which said individual belongs). This imputation is made as described below, either by
  regarding the position of each marker, genotyped and non genotyped, (which means that the imputation of genotypic data for each marker is done regarding the allelic value of consecutive markers from individuals of the said first population); or
  using an algorithm that is based on the prior knowledge of Linkage Disequilibrium and genotyping data of the first population, which doesn't need prior information on the of relative genetic position of such markers.

This method is of particular interest when there is a need to genotype a population of individuals that are all derived from the same parents or related to a given population, for which the genotyping information is available.

This method is, in particular, used in breeding programs in order to select the individuals presenting the best composition of alleles at different loci, and use them in further rounds of breeding.

The method makes use of the fact that recombination (crossing-over) is not very frequent. Consequently, when two consecutive markers have been inherited from a specific parent, it can be assumed that the region between these two markers originates from said specific parent. In this case, it is thus important to use an ordered set of markers, to perform the claimed method, as one needs to be able to position each marker with regards to the other ones The method is also of interest for applications that don't need any inputation, and can be performed to take advantage of the decrease in genotyping cost per individual observed when a multiplexed genotype of several individuals is performed.

One can genotype individuals from the second population with subset of markers and compare the percentage of common allele with some individual of the first population, that make it possible, in particular, to deduce the percentage of shared genome between individuals, for instance in a backcross application (known as the genome ratio of such individuals). For this kind of use, the set of marker can be an ordered one or not: in fact, the higher the number of markers genotyped for each individual, the less it is important to use an ordered set of markers, with prior knowledge on their relative genetic position, in the method of the invention.

Consequently use of an ordered set of markers is not a prerequisite for performing the method as described in this application.

The method according to the invention can be summarized as such:

The individuals are split in a given number (designated as "X") of subgroups, that may be called "population subgroups", or subgroups of individuals". It is preferred when said subgroups contain approximately the same number of individuals. This separation of individuals and allocation to a given subgroup may be done by giving a reference to each individual, so as to identify to which subgroup it is assigned.

For each subgroup, only a fraction of the markers used to genotyped the parents will be used, and no marker will be used for genotyping individuals in more than one sub-group of individuals.

In view of the above, the set of markers will also be split in as many subsets that there are of population subgroups, namely X. This will thus define X "markers subgroups" or "markers subsets". It is preferred when each markers subset contains approximately the same number of markers than the other ones. A specific marker shall be present only in one marker subset.

The markers can be allocated to a marker subset randomly, but preferably they can be attributed based on their order on the targeted region by allocating the first marker of the ordered set of markers to the first marker subset, the second marker to the second marker subset, applying the rule up to cover all marker subsets. This allows a regular and even distribution of markers along the target region in each marker subset.

It is thus very unfavorable if the markers of a specific markers subset spans only a portion of said region that is to be genotyped (such as only one chromosome in the case the whole genome is to be genotyped, or the like) and when this subset doesn't contain any marker that spans other regions of the DNA. This step of allocation of markers to subsets may be first performed, and it is then preferable to assess the content of each subset in order to determine whether the nature of the markers in said subset will lead to technical difficulties when using this subset of markers for genotyping (such as to avoid unspecific amplification if preparation of DNA is performed by PCR, in particular multiplex PCR).

After performing these two steps, are then defined X subgroups of individuals and X subsets of markers, with no marker belonging to two different subsets of markers. It is also preferred that an individual is assigned to only one subgroup of individuals, although this is not mandatory.

The next step is to bijectively link a subset of markers to a subgroup of individuals. The individuals in the subgroups will thus be genotyped using the markers that have been assigned in the linked subsets.

The DNA of individuals in the subgroups is then prepared. It is not done the conventional way, as reminded above (unspecific amplification), which is suitable when the whole set of markers is to be applied for genotyping. The DNA preparation of individuals is done so as to only amplify, for an individual, the loci that are recognized by the markers in the subset linked to the subgroup to which belongs this individual (loci of interest).

This selection of loci of interest may be performed, in particular, either by specific PCR amplification of each locus (it is possible to perform multiplexed PCR reactions).

It is also possible to capture the sequences of the loci of interest with baits either in liquid or in solid phases (this can be done with the Agilent SureSelect DNA Capture Array from Agilent (Santa Clara, Calif., USA) or the protocol developed by Roche NimbleGen, Inc. (Madison, Wis., USA) or others. Once these loci of interest have been captured and isolated, they can be amplified (using non-specific primers as there are no more unwanted loci), and genotyped.

An alternative way could be to protect the loci targeted by the markers from the linked markers subset, before performing a step of degrading DNA at the unwanted loci. This can be performed by using TALEN (Transcription activator-like effector nuclease) proteins that target the unwanted loci and will thus cut the genome at these locations. Non-specific amplification such as the one described for the Axiom® protocol can then be performed, as no DNA carrying the unwanted loci will be amplified due to the cut performed at said unwanted loci by the TALEN.

Whatever the method used, the result of this DNA preparation step will be to obtain, for each individual, a DNA composition or library (enriched DNA fraction) that is enriched in the loci corresponding to the markers of the markers subset linked to said individual's subgroup, and in which the loci corresponding to other markers are either absent or a dramatic minority.

In view of the above, it is clear that the consequence of this step of DNA preparation/enrichment in specific loci is that, applying genotyping on the whole set of markers to said enriched DNA fraction would only provide information on the alleles at said loci of interest, that have been enriched in said enriched DNA fractions, the other loci being absent or in a number below the noise detection threshold.

In the method of the invention, though, the step of revealing the nature of the alleles is performed after various enriched DNA fractions, each being from one individual of the different population subgroups, are pooled together, thereby leading to a multiplexed pool of loci. By construction, it is to be noted that each locus that is present in said multiplexed pool of loci originates only from one individual, in this embodiment.

This multiplexed pool of loci is then processed through conventional ways (such as through arraying or sequencing) in order to determine the allele at each locus.

It is then possible to allocate each allele to the individual from which the allele's locus originated (demultiplexing the results to link each determined allele to its marker and thus to the individual belonging to the subgroup of individual linked to the subset of markers from which said marker comes from).

By this method, it is thus possible to obtain genotyped individuals. These individuals are genotyped with only a subset of markers, though, and two individuals from different population subgroups do not share any markers in this genotyping method.

When the individuals that have been genotyped are related to a population of individuals that have already been genotyped with the ordered set of markers (or when they are issued from a cross between parents that have already been genotyped with the ordered set of markers), the method as disclosed above can advantageously be completed by the addition of a further step of allocating, for each individual, alleles at loci that have not been genotyped (the loci corresponding to the markers that were not associated with the subgroup to which said individual belongs).

Said allocation/imputation step is performed using the linkage disequilibrium information between markers obtained from the individuals of the genotyped population to which said individuals genotyped according to the method of the invention are related, and the information obtained for the loci genotyped for said individual. As reminded above, the identification of the nature of an allele at a given position makes it possible to predict the nature of the allele at a consecutive position due to the linkage disequilibrium.

In particular, if individuals are derived from a cross between two identified and genotyped parents, said allocation is performed by applying the following imputation algorithm a. If two consecutive identified alleles (and polymorphic between the two parents) for said individual are from the same parental origin (plant A), the region and alleles between these two markers are considered to be from the same parental origin than said markers (Plant A)

b. If two consecutive identified alleles for said individuals are from different parent origins,
 i. The alleles between said consecutive identified alleles that are identical between the parents are allocated as such
 ii. The alleles between said consecutive identified alleles that are not identical between the parents are indicated as with "no information"

c. In all the others questionable situations, it is postulated that no recombination between parents is the most probable situation.

d. For allocating alleles on the end of chromosomes or the end of genotyped regions: alleles are from the parent for which the closest polymorphic marker is present (it is thus postulated that no recombination between parents is the most probable situation).

If individuals are related or apparented to a population that have previously been genotyped with an non-ordered or an ordered set of markers, some softwares are able to input and allocate the missing markers based on the data from the linkage disequilibrium between consecutive marker in the genotyped population.

One can cite the following softwares, which are widely available to the person skilled in the art: Beagle (Browning and Browning 2007, Rapid and accurate haplotype phase inference for genome-wide associations studies. Am j Hum genet 81:1084-1097), fastPhase (Weigel et al., 2010 Prediction of unobserved single nucleotide polymorphisme genotype of jersey cattle using references panels and population-based imputation algorithms. Journal of Dairy Science 93(5), 2229-2238; Nothnagel et al., 2008, A comprehensive evaluation of SNP genotype imputation. Humain Genetics, 125 (2). 163-171; Calus et al., 2011, Imputation of missing single nucleotide polymorphism genotypes using a multi-variate mixed model framework. Journal of Animal science, 89(7), 2042-2049, IMPUTE (Marchini et al., 2007, A new multipoint method for genome-wide association studies by imputation of genotypes. Nat genet 39:906-913), or MACH (Li and Abecasis 2006, Mach 1.0: rapid haplotype reconstruction and missing genotype inference. Am J Hum genet S79:2290).

Due to the fact that all individuals (sample genotype individual and individuals of the related population) have common ancestors, this makes it possible to use the linkage disequilibrium between two consecutive markers computed in the population to predict genotyping data for missing markers on the sample genotyped individuals.

"Consecutive identified alleles" means the proximal identified allele on the genetic map. On a following list of genetically ordered markers mk1, mk2, mk3, mk4, if mk1 has been genotyped, mk2 and mk 3 are missing and mk4 has been genotyped, the consecutive identified alleles are alleles of mk1 and mk4.

Using this mean of allocating alleles to non-genotyped loci for individuals with known genotyped parent, and assuming that the number of crossing over is generally less than 5, or 4, or even 3 per chromosome per meiosis, it is possible to eventually obtain individuals for which it is generally possible to allocate alleles for at least 95% of the loci associated with the markers of said ordered set of markers.

In summary, the invention thus relates to a method for genotyping with a set of markers, a genome region in individuals of a first population, said method comprising the steps of:

a) splitting said first population into a given number "X" of first population subgroups, containing approximately the same number of individuals b) splitting said set of markers into said given number "X" of markers subsets, containing approximately the same number of markers c) Bijectively linking each marker subset to a population subgroup d) Preparing, in the population subgroups, the loci of the individuals of said population subgroup, wherein said prepared loci correspond to the markers of the markers subset linked to said population subgroup, thereby obtaining DNA fractions enriched in said loci e) Mixing the enriched DNA fraction of a particular individual of a population subgroup with the enriched DNA fraction of other individuals of other population subgroups so as to obtain a multiplexed pool of enriched DNA fractions, f) Revealing, for said multiplexed pool of enriched DNA fractions, the alleles for each locus present in said multiplexed pool of enriched DNA fractions g) Allocating each revealed allele to the individual from which the corresponding locus was obtained, h) Thereby obtaining individuals for which a genome region has been genotyped with subsets of said ordered set of markers.

In a preferred embodiment, said set of markers is an ordered set of markers.

In another embodiment, said individuals of said first population are related to a second population, and said region has already been genotyped with said set of markers (preferably ordered in this embodiment) in the individuals of said second population.

As intended herein, said genome region is a part of the genome of said individual. There is no limit on the size of the region, which can be continuous or not within the genome.

In a specific embodiment, said genome region is a part of a chromosome of said individuals. In this embodiment, it is preferred that the region is a continuous part of the chromosome.

In another embodiment, said genome region is a whole chromosome of said individuals.

In another embodiment, said genome region is parts of two or more chromosomes of said individuals.

In a further embodiment, said genome region is the whole genome of said individuals.

In a specific embodiment, said individuals of said first population are derived from a cross between known parents that have been genotyped with the global set of markers. In this embodiment, said parents are thus said individuals of said second population.

Preparation of the Loci

As indicated above, this step gives added value to the method according to the invention with regards to the prior art method.

Indeed, whereas the methods of the prior art generally prepare the whole genome of the individual to be genotyped, only a subset of loci will be prepared for each individual in the method according to the invention.

Since each individual has been put in a population subgroup, which is linked to a marker subset, the loci that will be prepared for each individuals are the one that bear the polymorphisms (alleles) that can be revealed by the markers of said linked subset (the loci of interest). The person skilled in the art thus understand that the loci of interest will all be the same for individuals belonging to the same subgroup, and that there are no identical loci of interest for individuals belonging to different subgroups.

This may be done by different techniques.

The DNA preparation may be performed, in particular by specific PCR amplification of said loci, using appropriately designed primers. This PCR reactions may be multiplexed in order to save time and money (i.e. amplification is performed in the same vial for multiple primers, using multiple pairs of primers).

Alternatively, it is possible to capture the loci corresponding to the markers contained in the markers subset allocated to said population subgroup with baits, or to protect the loci of interest and then performing a step of DNA degradation to eliminate all the unwanted loci, as disclosed above.

The output of this step will be to obtain an enriched DNA fraction for each individual, wherein said enriched DNA fraction contains the loci of interest for this individual.

The result is enriched DNA fractions where the loci for which the alleles can be revealed are the same for individuals that are in the same population subgroup.

A locus present in the enriched DNA fraction for an individual in a population subgroup can't be found in the enriched DNA fraction of an individual in another population subgroup. This is due to the fact that a specific locus is linked to a specific marker and a marker, which belong to a specific marker subset is thus linked to a unique population subset.

In a specific embodiment, this method of preparing the enriched DNA fractions also contains a step of adding a tag (or index) to each DNA fragment obtained for an individual. Such tags are described in the art (see in particular the Sample Multiplexing technique of Illumina®, San Diego, USA). Some kits are available on the market to do this sample tagging step (such as the Illumina TruSeq™). This extra layer of sample multiplexing based on the tagging can be applied when the genotyping is done through sequencing.

These tags will allow to further improve the potency of the method of the invention.

The tags are generally DNA fragments which are ligated to the products obtained after preparing the loci of interest. Multiple tags may be generated and will be revealed at the same time the alleles are revealed. This system works best when genotyping is performed by sequencing the enriched DNA fractions.

Depending on the number of available tags (Y), 1/Y individuals of each subgroup will be labeled by a given tag 1/Y individuals will be labeled by another tag, and so on.

Mixing the Enriched DNA Fractions

The next step is to mix enriched DNA fractions from different individuals so as to obtain a multiplexed pool of enriched DNA fractions.

When no tag has been added during the enriched DNA fractions preparation step, the multiplexed pool shall not contain enriched DNA fractions coming from different individuals that belonged to the same subgroup Consequently, the multiplexed pool contains multiple enriched DNA fractions each of them coming from an individual that belongs to a different subgroup. In other words, each population subgroup is represented only at most once in a given multiplexed pool of loci.

When tags have been added to individuals during the enriched DNA fractions preparation step, the multiplexed pool may contain more than one enriched DNA fraction coming from individuals belonging to the same subgroup, with the proviso that these enriched DNA fractions don't bear the same tag/label.

Revealing/Identifying the Alleles

In a preferred embodiment, said revealing step f) is performed on an array (which can also be called a chip). In another embodiment, said revealing step f) is performed through sequencing.

It is to be understood that the revealing step is performed according to methods known in the art.

When tags have been added to individuals during the enriched DNA fractions preparation step, the revelation step also comprises the step of revealing the tags.

Allocating the Alleles to the Individuals

Demultiplexing the genotyping data and allocating the alleles to the individuals from which the related loci were obtained is performed by any method, such as by hand or by using adequate software, as disclosed above.

Filling the Gaps/Obtaining Nearly Full Genotyping Information

The method of the invention provides genotyping information only for a subset of loci/markers for each individual.

In the case the genotyped individual is related to an already genotyped population, it is possible to "fill the gaps", i.e. to obtain allele information for most of the loci/markers that have not been genotyped for said individual (i.e. the loci/markers that were not in the marker subset linked to the population subgroup to which belonged said individual), based on the molecular markers linkage disequilibrium computed on related individuals of said second population that has been extensively genotyped (i.e. with the whole set of markers).

Consequently, it is possible to allocate, for each individual and for the loci for which no allele information was obtained in step f), allele information using the allele information available for the genotyped individuals of said second population.

Said allocation is performed using the imputation algorithm described above. It is also possible to specifically obtain genotyping information for a few loci for which the information can't be inferred or presenting a particular interest, by performing a genotyping assay for these loci.

In an embodiment, said individuals in said first population are heterozygous. It can be the case when said individuals are derived from a cross between parents.

In another embodiment, said individuals in said first population are homozygous. This may be the case when these individuals are doubled haploids. It is reminded that a doubled haploid (DH) plant is a plant obtained from regeneration of haploid cells having undergone chromosome doubling. Haploid cells are produced from pollen or egg cells or from other cells of the gametophyte, then by induced or spontaneous chromosome doubling, a doubled haploid cell is produced, which can be grown into a doubled haploid plant.

In yet another embodiment, some individuals in the first population are homozygous and other individuals are heterozygous.

The given number X (number markers subsets and of the population subgroups) is preferably less or equal to 10, more preferably less or equal to 8, more preferably less or equal to 7, more preferably less or equal to 6, more preferably less or equal to 5, more preferably less or equal to 4, more preferably less or equal to 3.

Said given number X is preferably more or equal to 2, more preferably more or equal to 3, more preferably more or equal to 4, more preferably more or equal to 5, more preferably more or equal to 6, more preferably more or equal to 7.

In one embodiment, said markers of said ordered set of markers are evenly distributed on said region. This means that the distance between two given consecutive markers is higher or lower of no more than 15%, more preferably 10% of the average distance between two consecutive markers.

In another embodiment, said markers of said set of markers are such that they cover at least one part of said genome region more densely than other parts. This embodiment is of particular interest if it is known that some parts of the genome are more prone to bear genes or loci of particular interest. Using a higher density of markers at the loci for these regions makes it possible to reduce the uncertainty that recombination (crossing-over) can give; and/or obtain more valuable information.

In a specific embodiment, the average genetic distance between two consecutive markers in a subset of markers is less or equal to 10 cM, more preferably less or equal to 8 cM, more preferably less or equal to 6 cM, more preferably less or equal to 5 cM.

In a specific embodiment, the average genetic distance between two consecutive markers in a subset of markers is more or equal to 2 cM, more preferably more or equal to 3 cM, more preferably more or equal to 4 cM, more preferably more or equal to 5 cM.

In a specific embodiment, the average genetic distance between two consecutive markers in a subset of markers is about 5 cM.

In a specific embodiment, the average genetic distance between two consecutive markers in the ordered set of markers is about 3 cM.

In a specific embodiment, the average genetic distance between two consecutive markers in the ordered set of markers is about 4 cM.

In a specific embodiment, the average genetic distance between two consecutive markers in the ordered set of markers is about 6 cM.

In a specific embodiment, said ordered set of markers comprises more than 5000 markers, preferably more or equal to 6000 marker, more preferably more than 7000 markers.

EXAMPLES

Example 1

Figure 1:
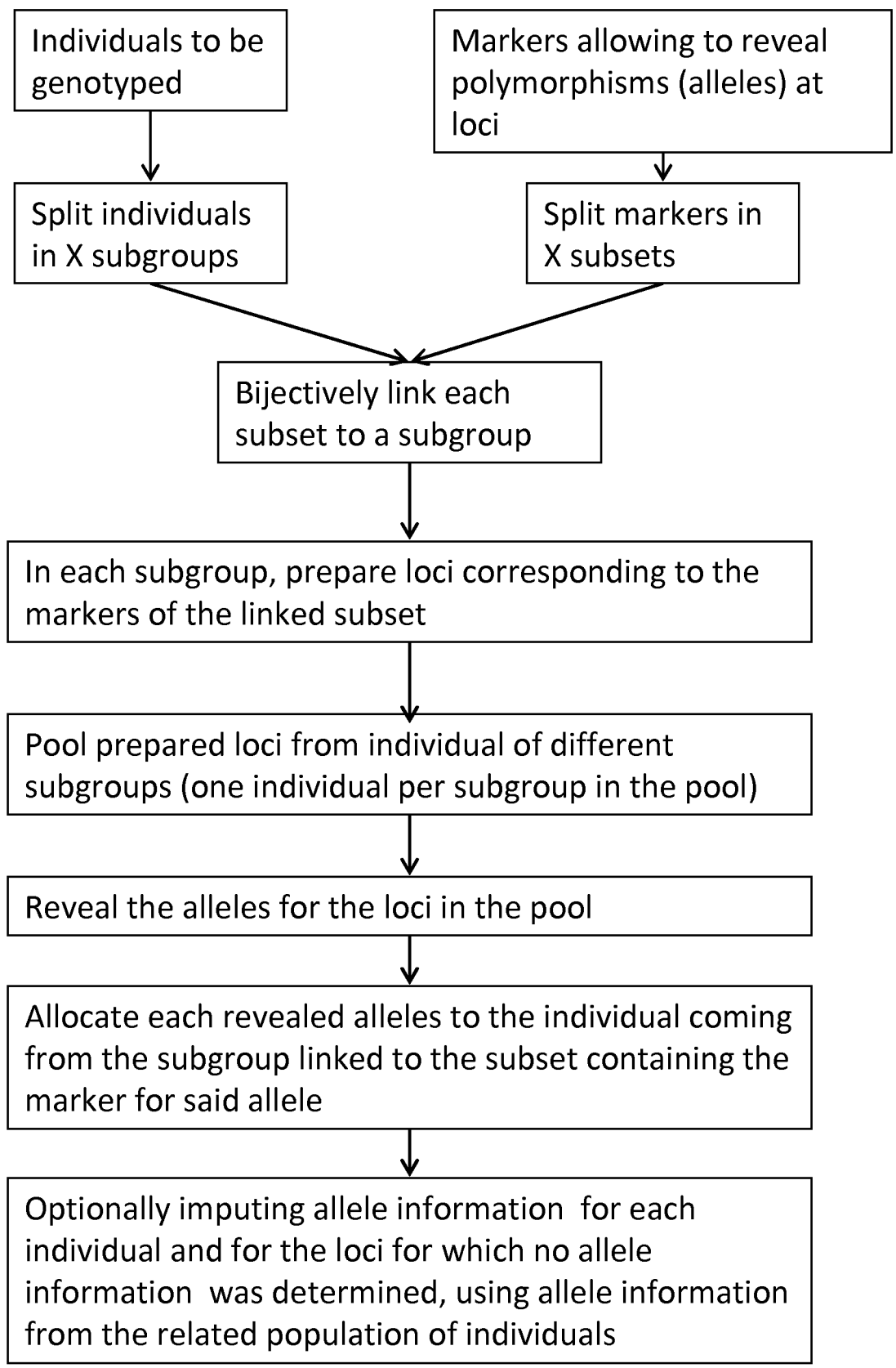
FIG. 1 summarizes the different steps for performing an embodiment of the method according to the invention FIG. 2 summarizes the different steps for performing another embodiment of the method according to the invention
Figure 2:
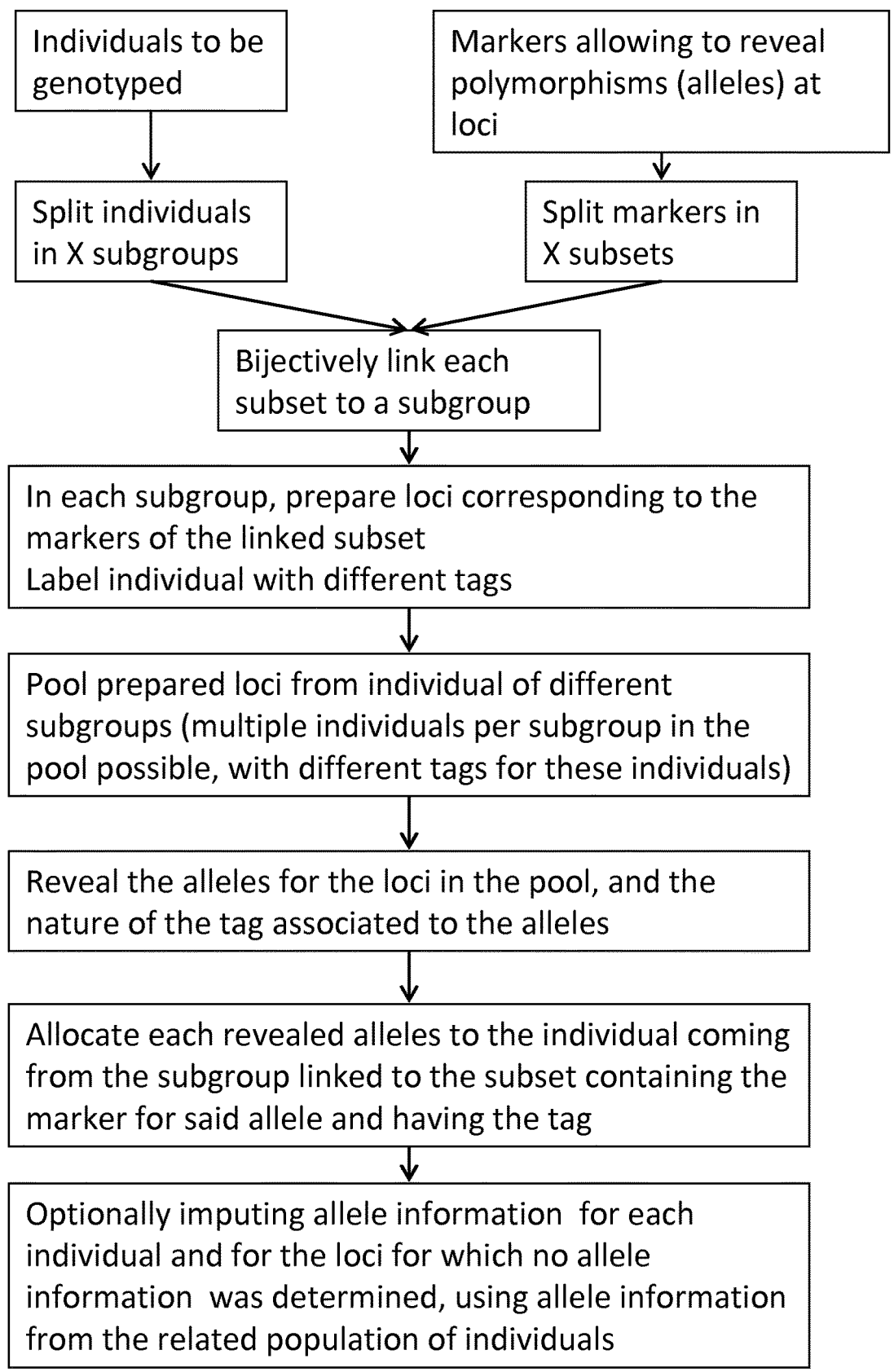

In this example, it is assumed that the predetermined number X is the number 4.
It is assumed that the population contains 8 individuals. These individuals are then split in 4 population subgroups (1 to 4), each subgroup containing 2 individuals.
It is also assumed that the ordered list of markers contains 20 markers designated as mk1, mk2 . . . mk20, according to their order in the list.
The set of markers is split in 4 subsets which will allow a multiplex of 4 samples.
The 4 sets of markers (if assumed that there are 20 markers) are:
    marker subset 1: mk1, mk5, mk9, mk13, mk17
    marker subset 2: mk2, mk6, mk10 mk14, mk18
    marker subset 3: mk3, mk7, mk11, mk15, mk19
    marker subset 4: mk4, mk8, mk12, mk16, mk20
In this example, the first marker of the list is placed in the first marker subset, the second marker in the second marker subset and so on.
And then the principle is to perform a selection of loci as follow:
    the loci corresponding to the SNP detected by the markers of the marker subset 1 are selected/enriched for each individuals of population subgroup 1
    the loci corresponding to the SNP detected by the markers of the marker subset 2 are selected/enriched for each individuals of population subgroup 2
    And so on . . . .
This selection/enrichment can be done for instance either by PCR amplification of each locus or by capturing corresponding sequences with baits. An alternative way could be to protect the targeted loci before performing a step of DNA degradation to eliminate all the unwanted loci.
After this locus selection/enrichment, the enriched loci of 4 individuals (one from each population subgroup) are bulked and genotyping is performed with the full set of markers, using regular methods in the art (such as through a sequencing protocol or in an array).
The genotyping data:
    corresponding to the marker subset 1 can be attributed to the individual from the population subgroup 1
    corresponding to the marker subset 2 can be attributed to the individual from the population subgroup 2 corresponding to the marker subset 3 can be attributed to the individual from the population subgroup 3 corresponding to the marker subset 4 can be attributed to the individual from the population subgroup 4

Example 2

In this example, it is assumed that the predetermined number X is the number 4.

It is assumed that the population contains 8 individuals. These individuals are then split in 4 population subgroups (1 to 4), each subgroup containing 2 individuals.

Each population subgroup is then further split in two sub-subgroups A and B (containing one individual).

The individuals in each sub-subgroup A will be tagged with tag "A".

The individuals in each sub-subgroup B will be tagged with tag "B".

Said tags may be polynucleotides as described by Illumina in the TrueSeq® kit.

It is also assumed that the ordered list of markers contains 20 markers designated as mk1, mk2 . . . mk20, according to their order in the list.

The set of markers is split in 4 subsets which will allow a multiplex of 4 samples.

The 4 sets of markers (if assumed that there are 20 markers) are:

marker subset 1: mk1, mk5, mk9, mk13, mk17
marker subset 2: mk2, mk6, mk10 mk14, mk18
marker subset 3: mk3, mk7, mk11, mk15, mk19
marker subset 4: mk4, mk8, mk12, mk16, mk20

In this example, the first marker of the list is placed in the first marker subset, the second marker in the second marker subset and so on.

And then one performs a selection of loci as follow:

the loci corresponding to the SNP detected by the markers of the marker subset 1 are selected/enriched for each individuals of population subgroup 1 the loci corresponding to the SNP detected by the markers of the marker subset 2 are selected/enriched for each individuals of population subgroup 2

And so on . . . .

In this example, the ultimate output is then 8 samples of DNA.

One DNA sample from an individual of population subgroup 1 (with loci revealed by the markers of the marker subset 1), said DNA tagged with tag A One DNA sample from an individual of population subgroup 1 (with loci revealed by the markers of the marker subset 1), said DNA tagged with tag B One DNA sample from an individual of population subgroup 2 (with loci revealed by the markers of the marker subset 2), said DNA tagged with tag A One DNA sample from an individual of population subgroup 2 (with loci revealed by the markers of the marker subset 2), said DNA tagged with tag B One DNA sample from an individual of population subgroup 3 (with loci revealed by the markers of the marker subset 3), said DNA tagged with tag A One DNA sample from an individual of population subgroup 3 (with loci revealed by the markers of the marker subset 3), said DNA tagged with tag B One DNA sample from an individual of population subgroup 4 (with loci revealed by the markers of the marker subset 4), said DNA tagged with tag A One DNA sample from an individual of population subgroup 4 (with loci revealed by the markers of the marker subset 4), said DNA tagged with tag B After this locus selection/enrichment, one shall bulk the enriched loci of the 8 individuals and perform genotyping with the full set of markers, using regular methods in the art (such as through a sequencing protocol, as described by Illumina for the TrueSeq® kit).

The nature of the tags (A or B) is also revealed at this stage, therefore allowing the determination of an relationship allele-label.

The genotyping data:

corresponding to the marker subset 1 with the tag "A" can be attributed to the individual from the sub-subgroup A of the population subgroup 1 corresponding to the marker subset 1 with the tag "B" can be attributed to the individual from the sub-subgroup B of the population subgroup 1 corresponding to the marker subset 2 with the tag "A" can be attributed to the individual from the sub-subgroup A of the population subgroup 2 corresponding to the marker subset 2 with the tag "B" can be attributed to the individual from the sub-subgroup B of the population subgroup 2 corresponding to the marker subset 3 with the tag "A" can be attributed to the individual from the sub-subgroup A of the population subgroup 3 corresponding to the marker subset 3 with the tag "B" can be attributed to the individual from the sub-subgroup B of the population subgroup 3 corresponding to the marker subset 4 with the tag "A" can be attributed to the individual from the sub-subgroup A of the population subgroup 4 corresponding to the marker subset 4 with the tag "B" can be attributed to the individual from the sub-subgroup B of the population subgroup 4

Example 3

In this example, the predetermined number is 6.

Therefore, one shall perform the method on bulks of 6 plants, using an ordered set of 6000 markers (thereby applying 1000 markers per plant).

Using 1000 (one thousand) markers for a map of 3000 cM signifies that the mean interval between two consecutive markers is 3 cM.

Assuming that there has been 30 crossing-over events per plant, 90 cM are expected to be not imputable (3% of the genome), when imputing the missing markers using the linkage disequilibrium or the genotyping information from the parents. This is a very low number, whereas the savings are high as 6 individuals can be genotyped in one single batch.

Information relating to the missing data can then be specifically obtained if needed.

Example 4

In this example, the predetermined number is 10.

Therefore, one shall perform the method on bulks of 10 plants, using an ordered set of 6000 markers (thereby applying 600 markers per plant).

Using 600 (six hundred) markers for a map of 3000 cM signifies that the mean interval between two consecutive markers is 5 cM.

Thus, assuming that there has been 30 crossing-over events per plant, 150 cM are expected to be not imputable (5% of the genome), when imputing the missing markers using the linkage disequilibrium or the genotyping information from the parents. This is a very low number, whereas the savings are high as 10 individuals can be genotyped in one single batch.

Information relating to the missing data can then be specifically obtained if needed.

Example 5

Goal:
Amplification by multiplex PCR in the same well of multiple loci corresponding to different markers, and genotyping on an Affymetrix® array.
Multiplex PCR:
Using the kit Qiagen 2× multiplex PCR and pooled PCR primers pairs, it was shown that it is possible to simultaneously amplify 126 regions/loci in the multiplex PCR.
For each locus, the distance between the primers is from 1 to 10 bases, the amplified region contains the polymorphism to genotype.
Protocol:

|  | Vol (µl) | Vol (µl) | Vol (µl) |
|---|---|---|---|
| Qiagen 2X Multiplex PCR Master Mix (PN 206145) | 2.5 | 5 | 25 |
| 5X STA Primers (252 primers at 250 nM) | 1 | 2 | 10 |
| DNase-free water | 0 | 0 | 0 |
| Volume mix | 3.5 | 7 | 35 |
| genomic DNA | 1.5 | 3 | 15 |
| Total | 5 | 10 | 50 |

PCR conditions are: 95° C. × 15 min + (95° C. × 15 s + 60° C. × 4 min) × 14 cycles + 17° C. (hold).

The PCR products have then been processed using the Axiom® technology of Affymetrix®, and the alleles have been revealed on an Affymetrix® array.

Figure 3:
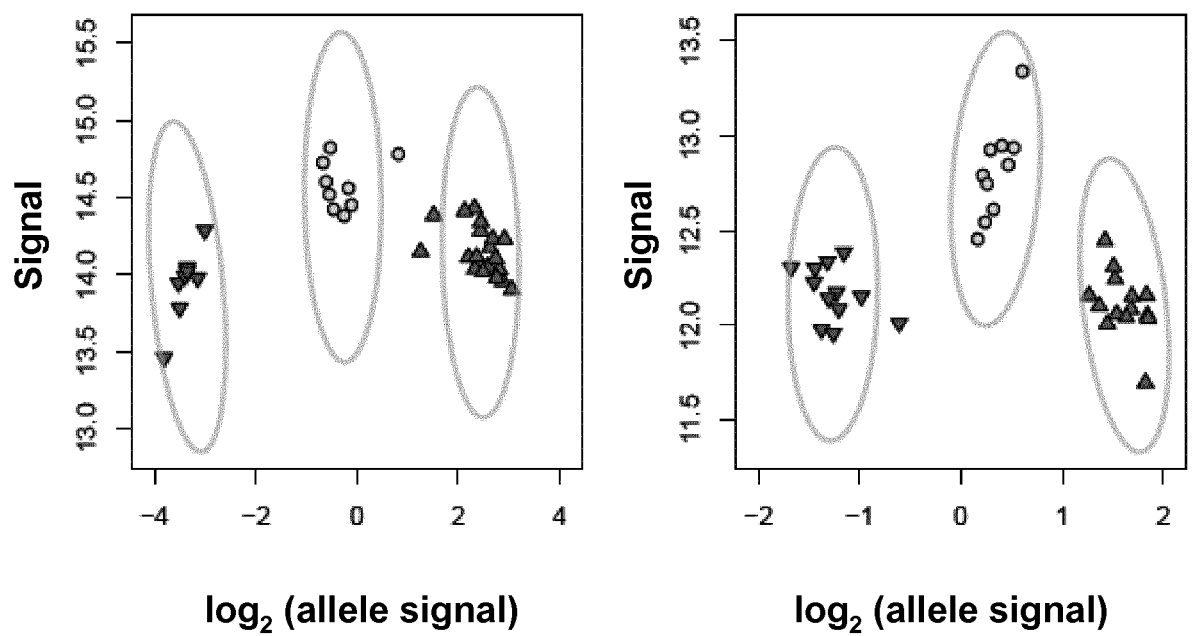
FIG. 3: Cluster separation in the log 2 (allele signal) obtained for two SNPs using the Axiom technology for samples that have been obtained through a multiplexed PCR. Each sample is shaped and colored according to called genotypes (bottom triangles, circles and up triangles corresponds to AA, AB, BB, respectively). Ovals are cluster position posterior results from the genotyping algorithm.

The results show that it is possible to obtain DNA samples enriched in specific loci. These samples can then be pooled and analyzed on the array. Results of genotyping for two of these markers are shows on the FIG. 3. This figure shows that, for the two SNPs of this figure, it has been possible to obtain a good separation of the different possible alleles, thereby demonstrating the possibility to conduct an appropriate genotyping when using an DNA fraction enriched in specific loci, obtained by a multiplex specific PCR amplification. Same kind of data was also obtained for other SNPs.

The invention claimed is:

1. A method for obtaining, in a population, individuals for which a genome region has been genotyped with a subset of markers, wherein the set of markers covers the genome region of the individuals, said method comprising the steps of:
   a) splitting said population into a given number "X" of population subgroups, containing approximately the same number of individuals,
   b) splitting said set of markers into said given number "X" of markers subsets, containing approximately the same number of markers, wherein a specific marker is present only in one marker subset,
   c) bijectively linking the markers subsets to the population subgroups, thereby assigning each of the marker subsets to a single subgroup of the population subgroups,
   d) preparing, in each of said population subgroups, the loci of the individuals of said population subgroup, wherein the prepared loci are the ones associated with the markers belonging to the markers subset that was assigned, in step c) to said population subgroup, thereby obtaining enriched DNA fractions, enriched in said loci for the individuals of the population, and wherein alleles can be discriminated at the prepared loci using the markers associated with the loci,
   e) mixing the enriched DNA fraction, obtained in step d), of a particular individual from one of the population subgroup, obtained in step a), with the enriched DNA fraction of other individuals from other population subgroups, that were obtained in step a), so as to obtain a multiplexed pool of enriched DNA fractions, wherein the multiplexed pool contains the loci of only one individual from each of the population subgroups,
   f) revealing, for said multiplexed pool of enriched DNA fractions, the alleles for each locus present in said multiplexed pool of enriched DNA fractions thereby obtaining revealed alleles,
   g) allocating each of said revealed alleles to the individual of the population subgroup linked to the subset containing the marker associated with the locus, and from which the enriched DNA fraction present mixed in the pool originates,
   h) thereby obtaining individuals for which a genome region has been genotyped with a subset of said set of markers.

2. The method of claim 1, wherein said set of markers is an ordered set of markers.

3. The method of claim 1, wherein said individuals of said population are derived from a cross between parents, or related to another population, wherein said region has already been genotyped with said set of markers in said parents or in the individuals of said other population, such said individuals thereby being genotyped individuals.

4. The method of claim 3, wherein said set of markers is an ordered set of markers and which further comprises the step of allocating, for each individual and for the loci for which no allele information was obtained in step f), allele information using the allele information available for said parents or for said genotyped individuals of said other population.

5. The method of claim 1, wherein step f) is performed on an array.

6. The method of claim 1, wherein step f) is performed through sequencing.

7. The method of claim 1, wherein individuals from the same population subgroup are individually indexed with various molecular tags.

8. The method of claim 1, wherein said markers of said set of markers are evenly distributed on said region.

9. The method of claim 1, wherein said markers of said set of markers cover at least one part of said genome region more densely than other parts of said genome region.

10. The method of claim 1, wherein said genome region is a part of a chromosome of said individuals.

11. The method of claim 1, wherein said genome region is a whole chromosome of said individuals.

12. The method of claim 1, wherein said genome region is the whole genome of said individuals.

13. The method of claim 1, wherein step d) is performed by PCR amplification of the loci corresponding to the markers contained in the markers subset linked to said population subgroup in step c).

14. The method of claim 1, wherein said preparation step d) is performed by capturing the loci corresponding to the markers contained in the markers subset allocated to said population subgroup with baits.

15. The method of claim 1, wherein said preparation step d) is performed by protecting the loci corresponding to the markers contained in the markers subset allocated to said population subgroup and performing a step of DNA degradation to eliminate all the unwanted loci.

* * * * *